US010721950B2

(12) United States Patent
Cecava et al.

(10) Patent No.: US 10,721,950 B2
(45) Date of Patent: Jul. 28, 2020

(54) PROCESS FOR REMOVAL OF MYCOTOXINS FROM INSOLUBLE PLANT-DERIVED PROTEIN

(71) Applicant: Archer Daniels Midland Company, Decatur, IL (US)

(72) Inventors: Michael J. Cecava, Monticello, IL (US); Perry H. Doane, Decatur, IN (US); Thomas V. Gottemoller, Corpus Christi, TX (US); Scott Tilton, Wichita, KS (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

(21) Appl. No.: 15/764,375

(22) PCT Filed: Sep. 12, 2016

(86) PCT No.: PCT/US2016/051277
§ 371 (c)(1),
(2) Date: Mar. 29, 2018

(87) PCT Pub. No.: WO2017/058501
PCT Pub. Date: Apr. 6, 2017

(65) Prior Publication Data
US 2018/0263264 A1    Sep. 20, 2018

Related U.S. Application Data

(60) Provisional application No. 62/234,296, filed on Sep. 29, 2015.

(51) Int. Cl.
*A23L 5/20*    (2016.01)
*A23J 3/14*    (2006.01)
*B01J 20/12*    (2006.01)
*C07D 493/14*    (2006.01)
*C07K 14/415*    (2006.01)

(52) U.S. Cl.
CPC .................. *A23L 5/273* (2016.08); *A23J 3/14* (2013.01); *A23L 5/27* (2016.08); *B01J 20/12* (2013.01); *B01D 2257/93* (2013.01); *C07D 493/14* (2013.01); *C07K 14/415* (2013.01)

(58) Field of Classification Search
CPC ..... A23L 5/27; A23L 5/273; A23J 3/14; B01J 20/12; B01D 2257/93; C07D 493/14; C07K 14/415
See application file for complete search history.

(56) References Cited

U.S. PATENT DOCUMENTS

| | | | | |
|---|---|---|---|---|
| 2012/0214897 A1* | 8/2012 | Yiannikouris | ........... | B01J 20/26 522/167 |
| 2013/0122143 A1* | 5/2013 | Davis | ...................... | A23L 5/273 426/18 |
| 2013/0164795 A1* | 6/2013 | Lowe | ....................... | C12P 7/16 435/134 |
| 2016/0374364 A1* | 12/2016 | Lee | ....................... | A23K 10/12 426/53 |

* cited by examiner

Primary Examiner — Anthony J Weier
(74) Attorney, Agent, or Firm — Andrew F. Nilles

(57) ABSTRACT

The present invention is directed to a process for the removal of mycotoxins from insoluble plant-derived protein using density-based particle separators. The end product contains a substantial portion of the proteins, including insoluble proteins, and a low concentration of mycotoxin. The process is particularly useful for removing aflatoxins from corn meal protein.

19 Claims, 7 Drawing Sheets

Process Flow Diagram

Fig 6. Weight loss from insoluble protein overs, %

3900 rpm on research decanter – approximately 1300 g ns from plant-derived insoluble protein

PROCESS FOR REMOVAL OF MYCOTOXINS FROM INSOLUBLE PLANT-DERIVED PROTEIN

CROSS-REFERENCE TO RELATED APPLICATIONS

This application is a national stage entry of International Application No. PCT/US2016/51277, filed Sep. 12, 2016, which itself claims priority to U.S. Provisional Patent Application No. 62/234,296, filed Sep. 29, 2015, each of the contents of the entirety of which are incorporated by this reference.

FIELD OF THE INVENTION

The present invention relates generally to the field of contaminant removal from food and feed ingredients derived from processing agricultural products, and more particularly to removing mycotoxins from insoluble protein products obtained from corn and peanut processing.

BACKGROUND OF THE INVENTION

Mycotoxins are naturally occurring secondary metabolites produced by different fungi and are known to contaminate many commonly grown crops. These toxins are known to impact growth performance and health of animals and humans that consume contaminated materials. Mycotoxins having the most impact on animal production include aflatoxins, deoxynivalenol, T-2 toxin, zearalenone, ochratoxin A, fumonisins, and ergot alkaloids. One of the most common of these is aflatoxin, a known toxin and potent carcinogen. It is produced during drought conditions, and results from the growth of *Aspergillus flavus* and/or *Aspergillus parasiticus*. Aflatoxin concentrations are highly regulated in both human and animal nutrition, as aflatoxin $B_1$ is one of the most potent hepatocarcinogens known. Ingestion of aflatoxins by livestock species is typically accompanied by a reduction in feed intake and a correlated reduction in growth rate.

Processing of agricultural commodities that have been contaminated with mycotoxins result in a concentration of the toxins in certain co-products and by-products and frequently these toxins concentrate in protein-containing streams. These toxins, while not intimately associated with the protein fractions, tend to follow these proteins during the normal processing schemes in place for grains and legumes. In the case of corn wet milling, many of these fungal toxins are concentrated in the corn gluten meal co-product, while concentrations remain lower in corn germ and corn fiber fractions. In contrast, the processed starch fraction is practically devoid of toxins. In the case of corn dry milling, toxins are concentrated in the distillers grains. This concentrating effect can result in toxin concentrations three (3) to ten (10) times that of the agricultural commodity prior to processing. Currently the United States Food and Drug Administration (FDA) Compliance Policy Guide Sec. 683.100 provides action levels for aflatoxins in animal feeds. Listed below are the FDA action levels for aflatoxins in animal feeds at the time of filing this application:

TABLE 1

Acceptable aflatoxin levels in animal feeds

| Aflatoxin, ppb | Uses |
| --- | --- |
| 20 | For corn and other grains intended for immature animals including immature poultry) and for dairy animals, or when its destination is not known |
| 20 | For animal feeds, other than corn or cottonseed meal |
| 100 | For corn and other grains intended for breeding beef cattle, breeding swine, or mature poultry |
| 200 | For corn and other grains intended for finishing swine of 100 pounds or greater |
| 300 | For corn and other grains intended for finishing (i.e. feedlot) beef cattle and for cottonseed meal intended for beef cattle, swine or poultry |

Corn gluten meal is one of the common co-product ingredients produced by corn wet mills that experiences a significant increase in mycotoxin concentration compared to the grain from which it was derived. As an example, the concentrating effects of aflatoxin in corn gluten meal results in greater than 20 ppb concentrations of aflatoxin on a dry weight basis when the incoming corn grain has almost negligible (<5 ppb) concentrations of aflatoxin. Contaminated corn gluten meal is substantially discounted when aflatoxin concentration is greater than 20 ppb resulting in significant financial loss for corn processing plants faced with mycotoxin challenges.

The animal feed industry has long been aware that bentonite products, hydrated sodium/calcium aluminosilicates (HCAS), and activated charcoals have adsorbing and binding characteristics with respect to certain mycotoxins and thus their use may alleviate mycotoxin effects on feed intake, growth or lactation performance of livestock. However, from a regulatory perspective, the act of adding a mycotoxin adsorbent to a contaminated feedstuff does not in itself guarantee that the mycotoxin contaminant is rendered harmless. Therefore, adding an adsorbent to a production process without removing the adsorbent and adsorbed toxin does not address the problems associated with the toxin. Additionally, the US FDA currently has not approved the use of mycotoxin adsorbent agents as feed ingredients, although several of the products commonly used for this purpose in other areas of the world are approved as flowability enhancers in the United States.

In an attempt to remediate toxins by adsorption, the United States Department of Agriculture developed a process to produce a detoxified peanut protein concentrate. In this process, a bentonite adsorbent and enzymes are used in peanut processing to limit the toxin concentration in a fractionated protein stream, as described in Davis, et. al. U.S. Pat. Pub. No. 2011/0014319 A1. In this approach, the clay is admixed with enzyme hydrolyzed peanut meal liquid followed by centrifuging to create a fraction containing a toxin-reduced soluble protein hydrolysate, and an insoluble protein containing the clay-adsorbed toxin. Whereas the soluble protein is recovered in the supernatant and is substantially free of aflatoxin and bentonite clay, the insoluble fraction containing the bentonite clay and toxin is substantially enhanced in toxin content. The insoluble protein fraction would therefore be restricted as a feed ingredient even if the toxin was ostensibly biologically inactivated via adsorption or not detectable using certain analytical techniques.

BRIEF SUMMARY OF THE INVENTION

The present invention is directed to a process for the removal of mycotoxins from plant-derived insoluble protein products exemplified by corn gluten or peanut meal that comprise primarily insoluble proteins. As used herein, an "insoluble protein product" and variations of the same means a product or feed stream obtained from processing an agricultural commodity wherein the majority of the protein present in the product is insoluble in water, so that the product is in the form of a slurry or suspension. The process comprises providing a feed or food comprising a plant-derived protein and a mycotoxin; forming a mixture comprising the feed or food and a mycotoxin sequestering agent; incubating the mixture to permit adsorption of said mycotoxin to the mycotoxin sequestering agent; and separating the mixture with one or more density-based particle separators to produce a first end-product and a second end-product, wherein the first end-product comprises at least eighty percent of said plant-derived insoluble protein.

In certain embodiments, the first end-product comprises ninety percent or more of the plant-derived protein contained in said ingredient. In some embodiments, the total amount of plant-derived protein in the first end-product is ninety-seven percent or more of the plant-derived protein contained in said ingredient.

In certain embodiments, the first end-product has a concentration of mycotoxin below legal limits that restrict its use in feed or food. The first end-product can have a concentration of mycotoxin that is less than 100 ppb, less than 50 ppb or safe for use in human food (i.e., less than 20 ppb in the United States).

In certain embodiments, the first end-product comprises no more than 50% of the mycotoxin in the feed, preferably no more than 20% and more preferably no more than 5%.

In certain embodiments, the mixture comprises up to 2% of the mycotoxin sequestering agent by weight, and the concentration of mycotoxin in the plant-derived protein in the ingredient is in excess of 5 ppb.

In certain embodiments, the process of the present invention uses plant-derived protein derived from a seed or grain. In some embodiments, the plant-derived protein is selected from the group consisting of corn gluten meal, peanut meal, cottonseed meal, distillers grains, wheat middlings, grain products, and mixtures thereof.

In certain embodiments, the mycotoxin sequestering agent is selected from the group consisting of activated carbon and adsorbent clays. In some embodiments, the clay is a bentonite or montmorillonite clay. In some embodiments the sequestering agent may contain a flocculating agent, or other activity enhancing compounds.

In some embodiments, the mycotoxin sequestering agent is between 0.25% and 5% by weight of said mixture, more preferably between 0.5% and 2% by weight of said mixture.

In certain embodiments, the density-based particle separators are selected from the group consisting of centrifuges, hydrocyclones and combinations thereof. More preferably, the density-based particle separators comprise one or more hydrocyclones possibly connected to a centrifuge, and the separating step comprises first separating the mixture in a series of hydrocyclones to produce a first hydrocyclone stream, comprising the first end-product, and a second hydrocyclone stream; and potentially further separating the second hydrocyclone stream in a centrifuge to produce a first centrifuge stream comprising a portion of the first end-product and a second centrifuge stream comprising the second end-product. In some embodiments, the hydrocyclone is operated between 20 psi and 300 psi. In some embodiments, the centrifuge is a decanter centrifuge and is operated to produce a force between at 300 and 3,600 g.

In some embodiments, the mycotoxin is an aflatoxin selected from the group consisting of aflatoxin $B_1$ ($AfB_1$), $B_2$, $G_1$, $G_2$ and combinations thereof. In other embodiments, the mycotoxin may consist of toxins such as ochratoxin, fumonisin, deoxynivalenol, zearalenone, aflatoxin, and combinations thereof.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENTS

The present invention is directed to a process for the removal of mycotoxins from agriculturally derived animal feed and human food ingredients wherein the majority of the protein present in the ingredient is insoluble plant-derived protein. The method operates without need to hydrolyze protein in the ingredient to form a soluble protein fraction such as may be accomplished by treatment with an enzyme as in the prior art. Exemplary ingredients include corn gluten and peanut meal, but the method is suitable for any agriculturally derived ingredient stream containing primarily insoluble proteins.

Figure 1A:
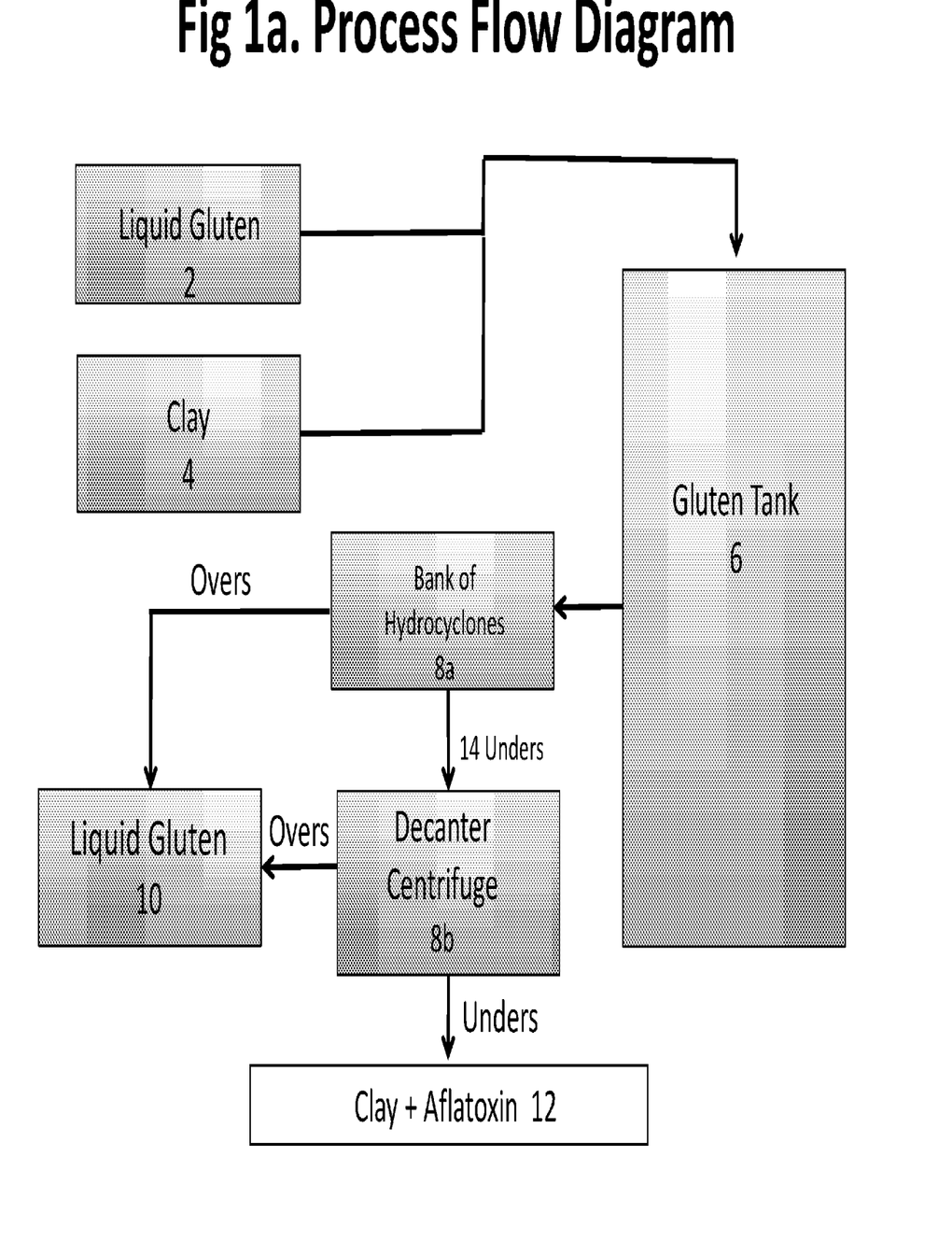
FIG. 1a is a process flow diagram consistent with one embodiment of the present invention.
Figure 1B:
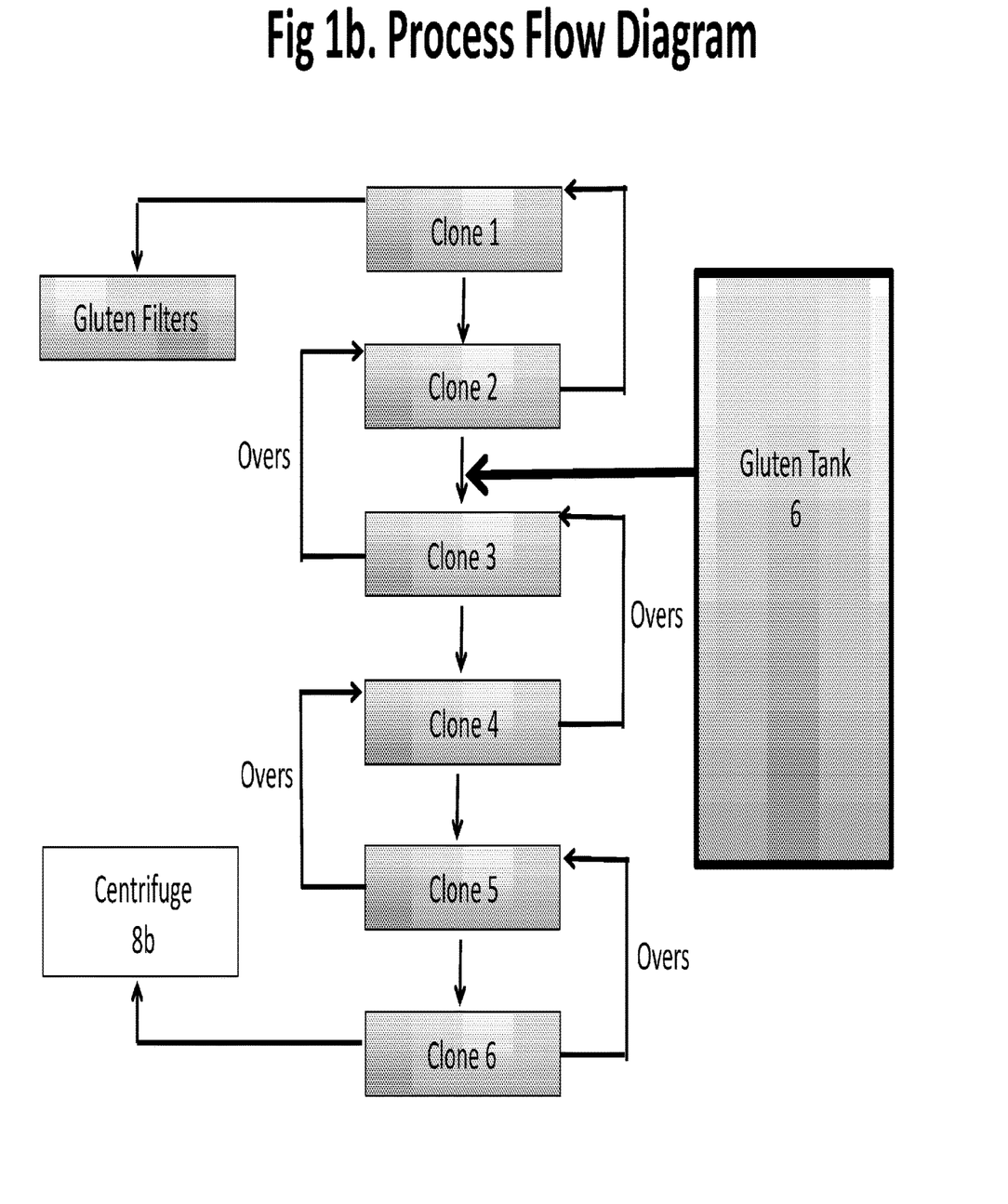
FIG. 1b is a process flow diagram consistent with one embodiment of the present invention.
Figure 2:
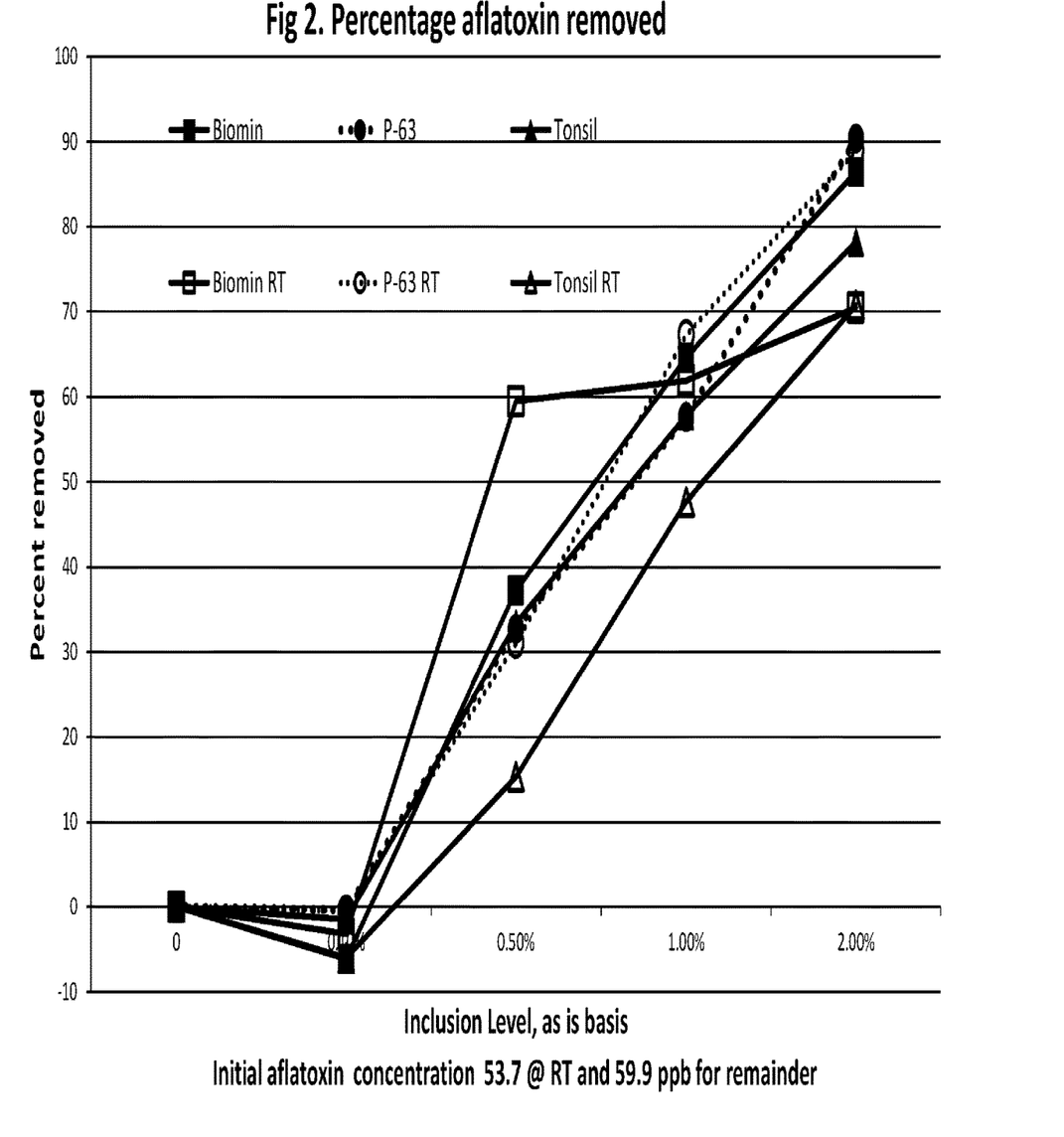
FIG. 2 is a dose response curve for three potential mycotoxin sequestering agents.
Figure 3:
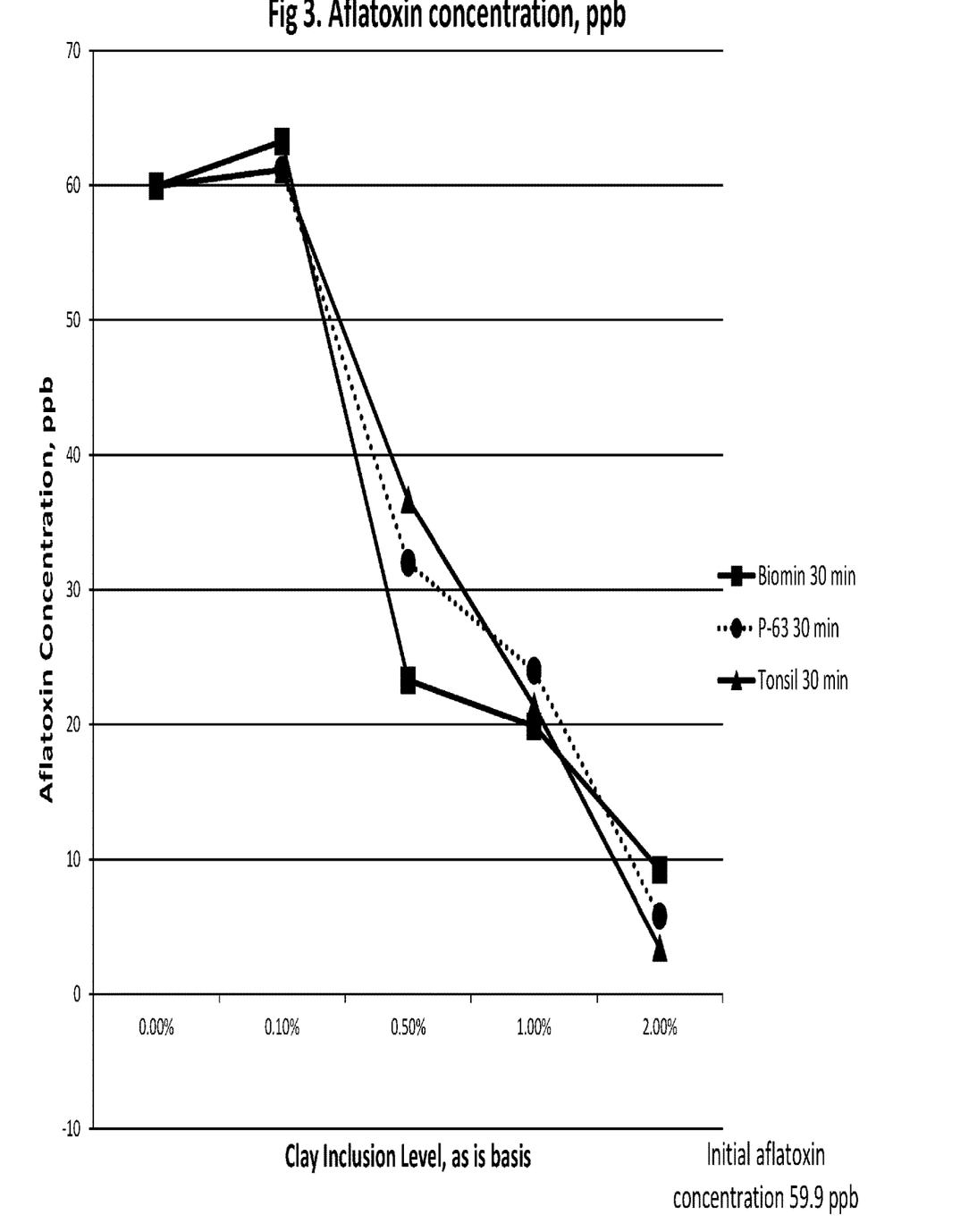
FIG. 3 shows the effect of addition of certain mycotoxin sequestering agents on the concentration of aflatoxin in corn gluten meal.
Figure 4:
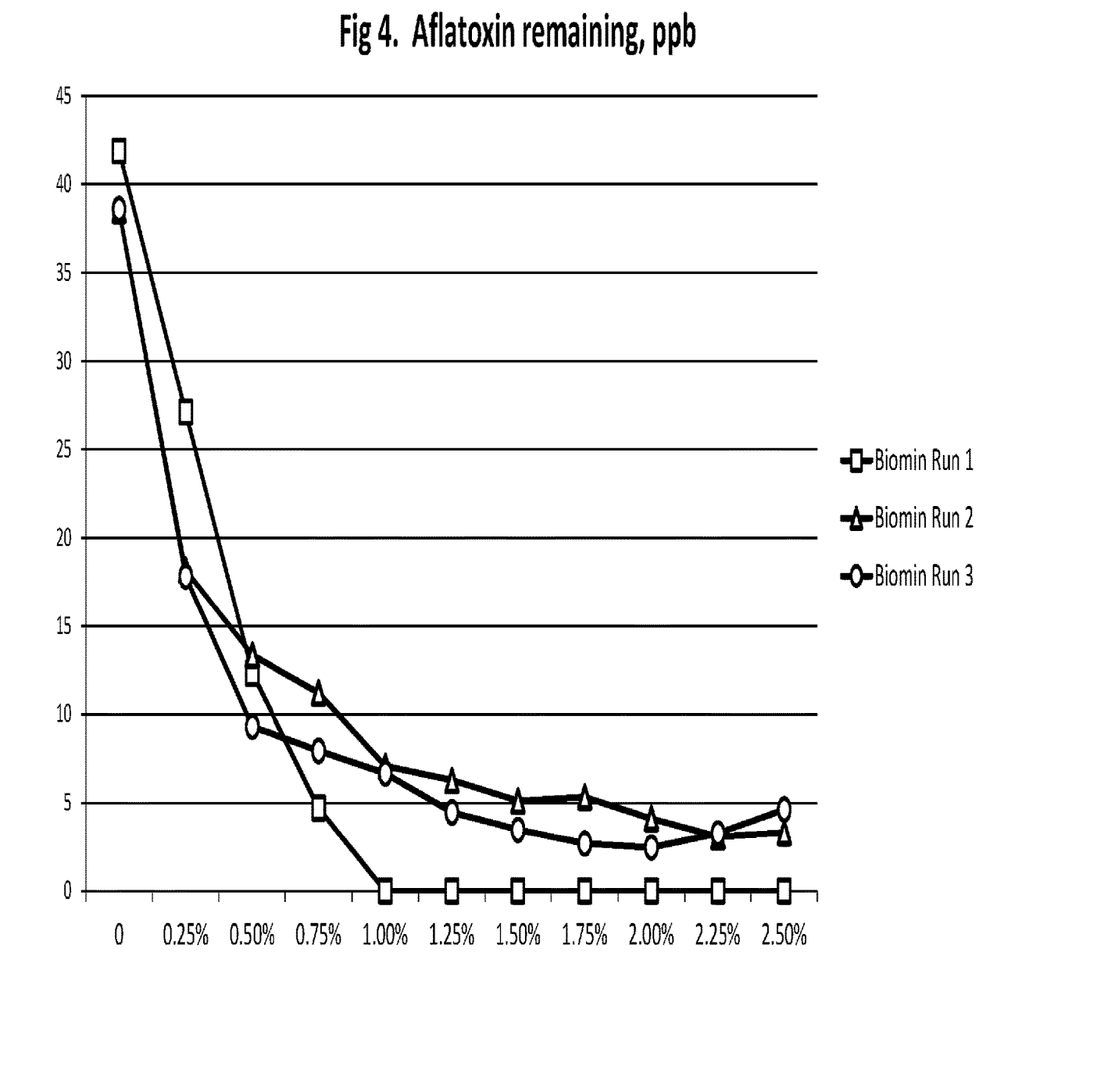
FIG. 4 is a dose response curve for 10 concentrations of mycotoxin sequestering agents.
Figure 5:
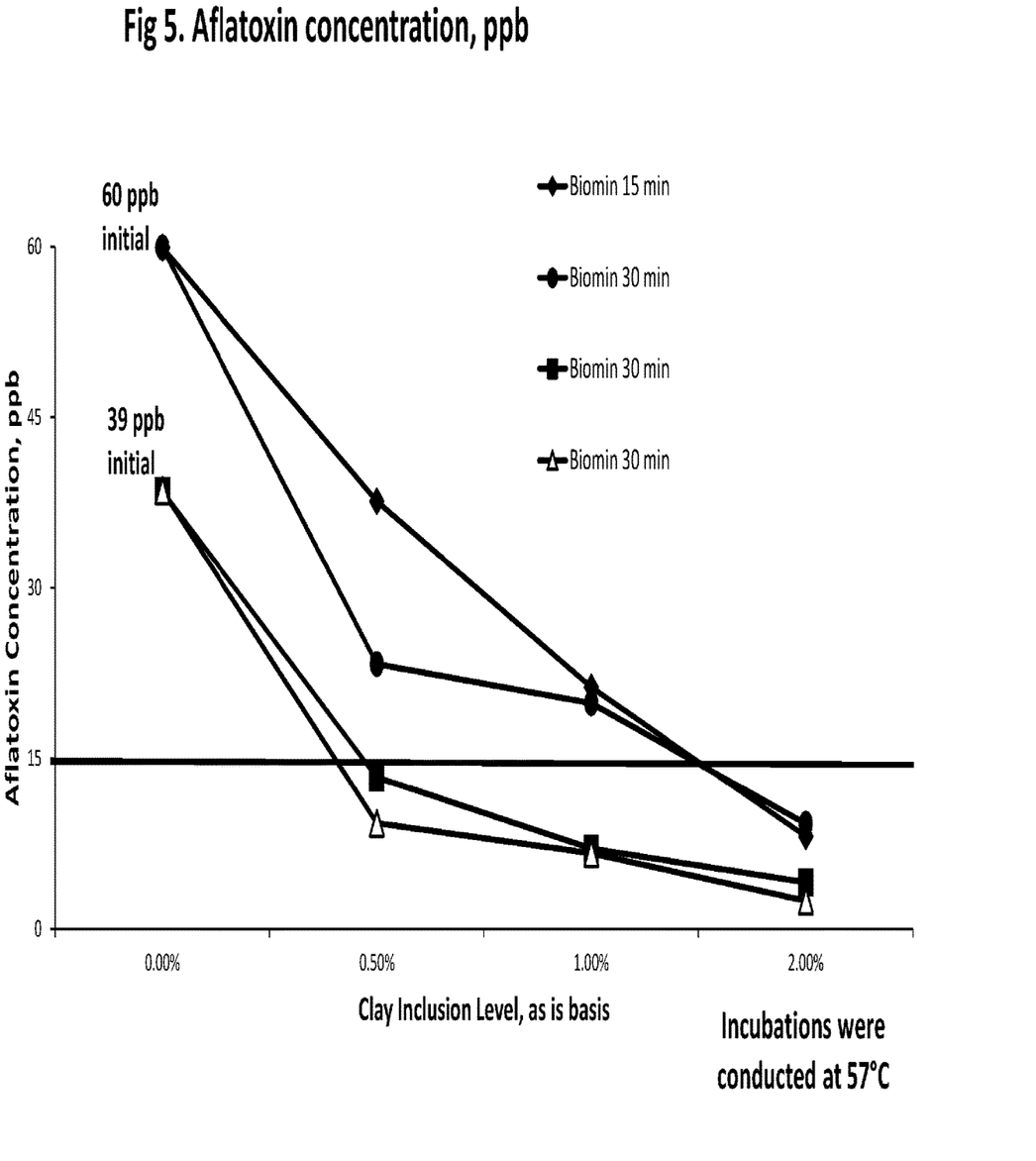
FIG. 5 is a dose response curve showing the effect of aflatoxin concentration in the feed.
Figure 6:
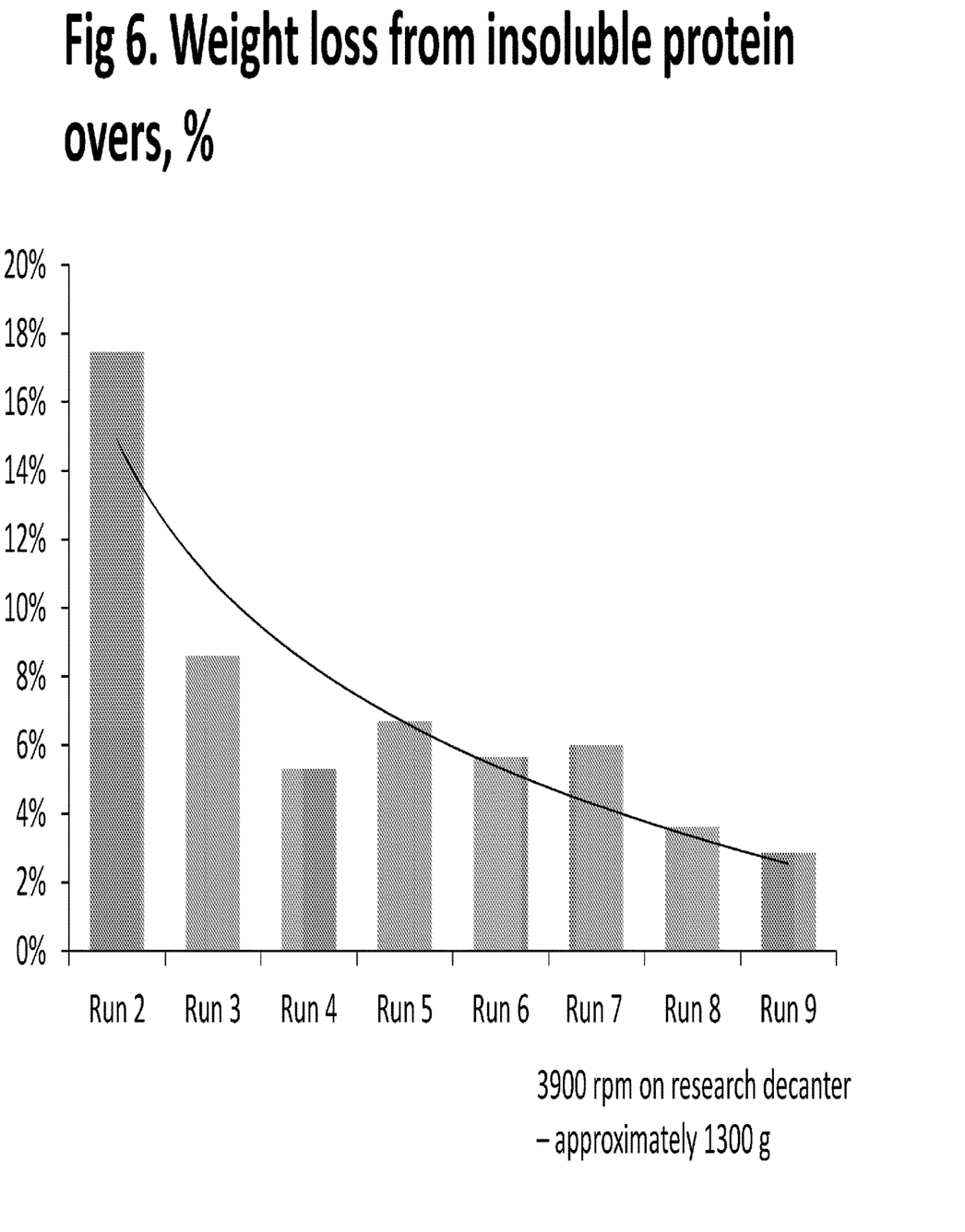
FIG. 6 is a bar graph showing the % of loss from the overs fraction after the separation from the unders fraction.

In one preferred embodiment depicted in FIG. 1a, an ingredient 2 comprising insoluble plant-derived protein and a mycotoxin is provided. The exemplary ingredient depicted in FIG. 1a is corn gluten, which is an insoluble protein enriched fraction derived from corn wet milling that is commonly obtained as a product stream in the form of a thick aqueous slurry or suspension. The ingredient is mixed with a mycotoxin sequestering agent 4 in a mixing tank, in-line mixer or other apparatus capable of blending solid and liquid ingredients. The mixture comprising the ingredient and the mycotoxin sequestering agent is incubated in the mixing tank 6 or other apparatus to permit adsorption of the mycotoxin contained in the insoluble plant-derived protein to the mycotoxin sequestering agent. The mixture comprising the ingredient and the mycotoxin sequestering agent is separated with one or more density-based particle separators 8a and 8b to produce a first end-product 10 and a second end-product 12. As depicted in FIG. 1a, the density based particle separators are hydroclones, which permit separation of the denser sequestering agent from the lighter insoluble protein in the suspension. As depicted in FIG. 1b, the mixture comprising the ingredient and the myctoxin sequestering agent flows through particle separators operated in series. A novel element of the process is the use of a counter-current flow whereby denser material is separated in a first pass and then lighter material is recycled through a second pass through the clone. In one embodiment the material is passed progressively through the series of hydroclones to achieve a concentration of the mycotoxin in the sequestering agent. In a preferred embodiment a minimum of three cyclings are employed to achieve concentration of the denser sequestering agent from the lighter insoluble protein. The separators are operated by normal procedures for processing of the ingredient with the only additional operational feature being that of a centrifuge (FIG. 1a, Item 8b) being used for dewatering of the clay and mycotoxin after being separated from the ingredient. As used herein, "first end-product" is defined as a fraction that comprises an insoluble plant-derived protein with a reduced concentration of mycotoxin and "second end-product" is defined as a fraction that comprises mycotoxin and a mycotoxin sequestering agent with a reduced concentration of insoluble plant-derived protein.

The process of the present invention allows a large percentage of the insoluble plant-derived protein to be retained in the first end-product and separated from the second end-product containing the mycotoxin and mycotoxin sequestering agent. This is beneficial because the mycotoxin concentration is substantially reduced in the insoluble plant-derived protein fraction rather than being concentrated in such fraction, as in the prior art. The resulting insoluble plant-derived protein containing material can be designated for consumption by animals, humans or both. The process of the present invention thus increases both the nutritional value and salability of insoluble plant-derived protein containing materials.

In a preferred embodiment, the process yields a first end-product comprising a significant portion of the insoluble plant-derived protein and a substantially reduced portion of the mycotoxin. While the dominant plant derived proteins present in grain processing are water insoluble proteins (e.g., zeins, corn processing) in most cases, the plant-derived protein streams contain some soluble proteins, therefore the invention is not limited to products where only insoluble proteins are present. Corn gluten, which is a zein enriched fraction separated from starch from corn endosperm is a well-known insoluble protein enriched stream obtained from corn wet milling operations and is commonly used in animal feeds.

A high percentage of the total protein solids content is collected in the first end-product obtained after separation of the mycotoxin sequestering agent. Preferably the first-end product comprises 50% or more of the total plant-derived protein contained in the ingredient. In a more preferred embodiment, the process yields a first end-product comprising 90% or more of the total plant-derived protein contained in the ingredient. In a most preferred embodiments, the process yields a first end-product comprising 97% or more of the plant-derived protein contained in the ingredient.

The process of the present invention can produce a first-end product having a concentration of mycotoxin that is below the concentrations considered as permissible by the U.S. F.D.A. for consumption by animals, humans or both. In a preferred embodiment, the first-end product has a concentration of mycotoxin less than 200 ppb on a dry weight basis. Other examples of concentrations of mycotoxin that can be achieved in the first end-product include less than 100 ppb or less than 20 ppb, on a dry weight basis. In a more preferred embodiment of, the first-end product has a concentration of mycotoxin less than 100 ppb. In a most preferred embodiment, the concentration of mycotoxin in the first end-product ranges from 0 ppb to 20 ppb. In certain aspects of the invention, the percentage of mycotoxin removed from the feed by the sequestering agent is 15% to 100%. In some preferred embodiments, the mycotoxin fraction removed from the feed is at least 30%, and can be at least 45%, at least 60%, at least 74%, at least 80% and at least 90%, such that the percentage of mycotoxin in the ingredient retained in the first end-product would be no more than 70%, no more than 55%, no more than 40%, no more than 26%, no more than 20% and no more than 10%, respectively.

The process of the present invention can be used to separate mycotoxins from a wide variety of materials comprising insoluble plant-derived proteins. In a preferred embodiment, the plant-derived protein is derived from a seed or grain. In certain embodiments, the plant-derived protein is derived from a by-product or co-product of industrial processing that contains high levels of insoluble plant-derived proteins. One such process is corn wet milling, wherein the corn gluten meal co-product contains a significant amount of insoluble plant-derived protein that could be used for more valuable commercial purposes if separated from the mycotoxin. In certain preferred embodiments, the plant-derived protein is purified corn gluten, corn meal, gluten enriched corn meal (i.e., corn meal gluten), peanut meal, cottonseed meal, wheat middlings, and mixtures thereof. In one preferred embodiment, the plant-derived protein is corn meal gluten. Other co-products and by-products suitable as ingredients for mycotoxin removal in accordance with the present invention include, but are not limited to corn fines, distillers grains, distillers grains with solubles, and corn dry mill solubles.

In addition, the process of the present invention can be used to remove a wide variety of mycotoxins. In certain embodiments, the mycotoxin to be removed is an aflatoxin, ochratoxin, fumonisin, deoxynivalenol, zeralenone, citrinin, T2-toxin, cyclopiazonic acid, or combinations of two or more of these toxins. In one preferred embodiment, including certain embodiments wherein aflatoxin is removed from corn meal, the aflatoxin may be selected from the group consisting of aflatoxin $B_1$ (AfB$_1$), $B_2$, $G_1$ and $G_2$.

The ingredient streams processed in the present invention preferably have a high liquids content. In a preferred embodiment, the ingredient stream comprises at least 50% liquids and no more than 50% plant-derived solids by weight. Preferably, the ingredient used in the present invention comprises between 5% and 30% plant-derived material and between 70% and 95% liquid by weight. In a most preferred embodiment, the ingredient comprises between 15% and 25% plant-derived material by weight.

Plant-derived protein ingredients with a wide range of concentrations of mycotoxin may be treated with the process of the present invention. In one embodiment, plant-derived proteins with a concentration of aflatoxin ranging from 20 ppb to 1,000 ppb on a dry weight basis may be treated. In certain preferred embodiments, aflatoxin concentrations of 10 ppb to 250 ppb are treated with the process. All aflatoxin concentrations are expressed in ppb are on a dry solids basis, unless otherwise indicated.

Mycotoxin sequestering agents are well-known in the art and a variety of mycotoxin sequestering agents are suitable for use in the present invention. In one embodiment, the mycotoxin sequestering agent is selected from the group consisting of adsorbent clay, hydrated sodium/calcium aluminosilicate, zeolite, and activated charcoal. In one preferred embodiment, the mycotoxin sequestering agent is an adsorbent clay. In a more preferred embodiment, the mycotoxin sequestering agent used is a bentonite clay, which is itself an adsorbent clay. The bentonite clay used in certain preferred embodiments may contain a flocculating agent or other activity enhancing compounds known in the art. In certain embodiments, mycotoxin sequestering agents suitable for use in the present invention are selected from the group consisting of but not exclusive to Biomin MycoFix Secure, Sud Chemie Ex Mex 1575, Sud Chemie Tonsil Supreme 536FF, Sud Chemie Sudfloc P-63 and Sud Chemie Sudfloc P-290.

The terms "adsorbent clays", "clay minerals", "mineral clay" or "clay", as used herein, are defined as any of a complex group of finely crystalline to amorphous, essentially hydrated aluminum silicate minerals of tectosilicate and phyllosilicate origin having the generalized formula $Al_2O_3SiO_2.xH_2O$, characterized by small particle size, cation exchange capability, and/or the ability to adsorb water and certain organic compounds, such as, but not limited to, aflatoxin, fumonisin, ergovaline, and mycotoxins. Minerals and vitamins may also be adsorbed to these clays. The most common mineral clays belong to the kaolinite, smectite, allophone, vermiculite, interstratified clays and illite groups including, but not limited to, the montmorillonite, attapulgite and bentonite groups. The terms "clay minerals", "adsorbent clay" or "clay" may also include, but is not limited to, natural tectosilicate minerals of the zeolite group and the synthetic zeolites or sodium calcium silicoaluminates. The term "aluminosilicate clay", as used herein, is defined as comprising a combination of silicate and aluminate in the form of a mineral clay and hydrated sodium/calcium aluminosilicates. The term "kaolinite", as used herein, is defined as one member of the group of common aluminosilicate clays. The mean particle size and variability of the particle size affect handling properties and functionality of clays. Clays providing efficacious sequestering of mycotoxins which are separable by mechanical operations from liquid media and insoluble proteins are desirable. In a preferred embodiment, the clay will have a mean particle size of no more than 500 um. Preferably, the clay used in the present invention will have a mean particle size between 10 and 200 um with a standard deviation of no more than 1× the mean. In a most preferred embodiment, the mean particle size of the clay will be <100 um with a standard deviation of no more than 1× the mean.

Mycotoxin sequestering agents may be used in a wide range of concentrations.

The amount of mycotoxin sequestering agent will depend, in part, on the type and quantity of mycotoxin. In one embodiment, the concentration of mycotoxin sequestering agents can range from between 0.5% and 5% by weight of the total ingredient mixture inclusive of water, more preferably between 0.5% and 1% and still more preferably 1% or less. In one exemplary embodiment the mycotoxin is aflatoxin, it being present in the plant-derived protein ingredient at a concentration of up to sixty parts per billion (60 ppb). In such exemplary embodiments\, the corresponding mixture for removal of the aflatoxin preferably comprises 2% mycotoxin sequestering agent by weight. In another preferred embodiment, the concentration of the aflatoxin in the plant-derived protein is up to forty-five parts per billion (45 ppb). In such an embodiment, the corresponding mixture preferably comprises 1% mycotoxin sequestering agent by weight. In another preferred embodiment, the concentration of the aflatoxin in the insoluble plant-derived protein in the final feed is between forty parts per billion (40 ppb) and forty-five parts per billion (45 ppb). In such embodiments, the corresponding mixture preferably comprises 1% mycotoxin sequestering agent by weight.

The process of the present invention may be performed on a batch basis. Most preferably, however, the process is performed on a continuous basis. In a continuous process, a temporary storage tank or mixing tank is used in the mixing and incubating steps of the process to allow for the mixture to be incubated for a time sufficient to permit adsorption of mycotoxins to the mycotoxin sequestering agent.

The mixture used in the process may be incubated for a range of times and at a range of temperatures. In one embodiment, the mixture may be incubated for a time between 5 minutes and 5 days and at a temperature between 5° C. and 90° C. In a preferred embodiment, the mixture may be incubated for a time between 10 and 60 minutes and at a temperature between 10° C. and 80° C. In another preferred embodiment, the mixture is incubated for between about fifteen (15) and forty (40) minutes and at a temperature between 15° C. and 60° C. In the most preferred embodiment, the mixture is incubated for about thirty (30) minutes at a temperature of about fifty-seven degrees Celsius (57° C.).

The components of the first end-product may be separated from the components of the second end-product using various types, arrangements and quantities of density-based particle separators. The process is operated under conditions that allow a substantial portion of the insoluble plant-derived proteins to be retained in the first end-product and separated from the mycotoxins and mycotoxin sequestering agent retained in the second end-product. In one embodiment, the mixture is separated with a centrifuge resulting in a first-end product fraction containing a large portion of the protein, including insoluble proteins, and a second-end product in the pellet fraction containing a large portion of the clay and mycotoxin. The centrifuge is operated between 100 and 10,000 g, or more preferably between 300 and 8000 g, and typically between 1000 and 5000 g. In a more preferred embodiment as shown in FIG. 1a, rather than a centrifuge, the mixture is first separated with one or more hydrocyclones (8a) to produce a first hydrocyclone stream or streams, comprising a first-end product, and a second hydrocyclone stream (14), liquid, clay, mycotoxin and minimal concentration of protein. The hydrocyclones are operated between 20 and 300 psi. The individual first hydrocyclone streams may be combined to form a single first hydrocyclone stream after passing through one or more hydroclones in series. The second hydrocyclone stream may be further separated in a centrifuge (8b) to produce a first centrifuge stream comprising additional first end-product and a second centrifuge stream comprising the second-end product. The first centrifuge stream is combined with the first hydrocyclone stream. The centrifuge is operated between 100 and 10,000 g. In one preferred embodiment, the mixture is first separated with 2 to 8 hydrocyclones in series.

The first end-product and second-end product can be further processed using techniques known in the art. For example, the first end-product can be delivered to a gluten filter before further processing into a desired product, such as animal feed. In certain embodiments, the second end product can be processed for use in fertilizer, recycled or disposed.

Certain research results and exemplary embodiments are illustrated by the following examples ranging from benchtop to pilot scale application.

In the following examples, the starting material was liquid corn gluten protein from a corn wet milling process, having a solids content of about 18.5% and a pH of approximately 3.8. The majority of the corn gluten protein in the material was insoluble protein.

EXAMPLE 1

An adsorbent clay sold as Biomin Biofix Secure (bentonite/dioctahedral montmorillonite) was obtained from Biomin Holding GmbH. The clay was added on a 1% by weight basis to liquid corn gluten protein suspension, having a 18.5% solids content. The corn gluten had 4.9 ppb aflatoxin concentration on a dry basis.

The mixture was manually shaken for 10 minutes at room temperature and centrifuged at 5000×g for 15 minutes to separate gluten meal protein from the clay. This process resulted in three layers after centrifugation, a solid clay pellet, a high moisture gluten cake layer, comprising about 50% solids, and a liquid supernatant layer. The gluten cake layer had an aflatoxin concentration of 3.04 ppb, which was a 35% reduction in aflatoxin concentration, notwithstanding the fact that the corn gluten already had an extremely low aflatoxin concentration. The control maintained an aflatoxin concentration of 4.93 ppb.

EXAMPLE 2

Experiment 1 resulted in three layers after centrifugation, a solid clay pellet, a high moisture gluten cake layer and a liquid supernatant. Experiment 1 was repeated using centrifuge speeds of 3000×g, 1500×g and 750×g for 10 minutes. For all centrifuge speeds, a clay pellet, a gluten meal cake layer, and a liquid supernate layer were formed.

EXAMPLE 3

Seven unique clay or clay-based ingredients with varying particle sizes were separately tested to ascertain their adsorption characteristics. Each clay was added on a 1% w/w basis to 100 ml liquid corn gluten having an 82% liquid content and an aflatoxin concentration of 12 ppb on a dry weight basis. The mixture was incubated while shaking for 15 minutes at 57° C. and subsequently centrifuged at 1500×g for 10 minutes to separate gluten protein from the clay. This resulted in a liquid supernatant, high moisture gluten cake and clay pellet. The supernatant was decanted and the gluten meal cake was tested for aflatoxin content [sum of aflatoxin B1, B1, G1 and G2, with results corrected to a dry matter basis for all samples.] The results are summarized in Table 2.

TABLE 2

Effect of various products on removing aflatoxin from liquid corn gluten protein*

| | Total Aflatoxin, ppb | Percent Removal, % |
|---|---|---|
| Control | 30.97 | 0.00 |
| Biomin BioFix Secure | 2.43 | 92.16 |
| Oil-Dri L-13-186 | 26.28 | 15.15 |
| Oil-Dri L-13-187 | 16.80 | 45.74 |
| Oil-Dri L-13-188 | 27.98 | 9.65 |
| Sud Chemie Ex Mex 1078 | 5.89 | 80.98 |
| Sud Chemie Ex Mex 1575 | 8.03 | 74.07 |
| Sud Chemie Ex Mex 1717 | 24.35 | 21.36 |

*Initial aflatoxin concentration 30.97 ppb. All products added at 1% of liquid mass and incubated for 15 minutes at room temperature A key finding was that surface area of the aflatoxin sequestering agents was important: a coarse, granular clay (Oil-Dri experimental product L-13-186), failed to adsorb aflatoxin. A second key finding was that a clay containing a flocculating agent, in addition to the clay may leave unacceptable residue in the gluten protein layer. A third key finding was that certain clays are preferred under the processing conditions tested. Following this process, the liquid corn gluten had an overall reduction in aflatoxin concentration ranging from 15% to 92%.

EXAMPLE 4

Dose titration of the top three performing clays from the first three experiments were performed to determine the preferred concentration, or range of concentrations, by weight of each clay agent that could elicit reduction of aflatoxin in liquid corn gluten protein. Clays were mixed with gluten liquid at concentrations of 0, 0.10%, 0.50%, 1.00% and 2.00% w/w liquid corn gluten having an 18.5% solids content and with an aflatoxin concentration of 53.7 ppb (ambient temperature samples) and 59.9 ppb (57° C. samples). The mixtures were incubated with agitation for 15 minutes and subsequently centrifuged at 1500×g for 10 minutes to separate corn gluten protein from the clay-aflatoxin product. The results are summarized in FIG. 2. Temperature did not affect aflatoxin adsorption but there was a strong relationship between clay age and preferred dosage.

EXAMPLE 5

A second dose titration experiment was performed with 3 of the clay agents using liquid gluten protein (18.5% solids) with an aflatoxin concentration of 59.9 ppb on a dry solids basis. Each clay agent was added at a concentration of 0, 0.10%, 0.50%, 1.00% and 2.00% w/w liquid corn gluten protein. The mixtures were incubated with agitation for 30 minutes at 57° C. and subsequently centrifuged at 1500 g for 10 minutes to separate corn gluten protein from the clay-aflatoxin product. The results are summarized in FIG. 3.

EXAMPLE 6

Further dose titration was conducted using one of the clays. Dosages used to conduct the research were 0.00%, 0.25%, 0.50%, 0.75%, 1.00%, 1.25%, 1.50%, 1.75%, 2.00%, 2.25%, and 2.50%. Three separate gluten protein samples were utilized containing 41.9, 38.5, and 38.6 ppb aflatoxin Samples and other processing conditions were consistent with Example 5. Results are summarized in FIG. 4.

A curvilinear response was observed with all three tests showing less that 15 ppb aflatoxin with the inclusion of 0.50% clay, but with the plateau occurring between 0.75 and 1.00% inclusion. Combined with the results from other experiments, it appears that inclusion of 1.00% of clay was particularly useful with the toxin levels evaluated in the process.

EXAMPLE 7

The effect of the initial concentration of aflatoxin in liquid corn gluten protein was also analyzed. Two discrete samples of liquid corn gluten protein were analyzed to contain 39 ppb and 60 ppb aflatoxin on a dry matter basis, respectively. Both sample batches had solids content of 18.5% and were incubated with agitation at 57° C. in the presence of 0.50%, 1.00% or 2.00% by weight of the clay, initially for 15 mins After other work, 30 minutes appeared more appropriate and samples were incubated with clay for 30 mins, twice with the second sample of liquid gluten. After incubation, samples were centrifuged at 1500 g for 10 minutes. The results are summarized in FIG. 5. The results demonstrate a strong dose-response relationship with greater aflatoxin removal with increasing dosage of clay.

EXAMPLE 8

Corn gluten protein was tested with pilot scale production equipment to test the laboratory concepts developed in previous experiments. The adsorbent clay was added on a 1.0% by weight basis to corn gluten with 18.5% solids content. The mixture was incubated at a temperature of 57° C., with a retention time of approximately 38 minutes with agitation, and passed to a Westphalia CA 150-01-33 two-phase decanter centrifuge operating at 3900 rpm, or approximately 1300×g. The overs fraction containing the insoluble corn gluten protein was separated from the unders fraction containing the clay and aflatoxin. The results are summarized in FIG. 6. Results were obtained in which more than 97% of the corn gluten protein was retained in the overs fraction, and less than 3% was found in the unders fraction.

EXAMPLE 9

An investigations was conducted to determine whether clays could be efficiently separated from liquid gluten using pilot scale processing. Liquid corn gluten meal was obtained from the Decatur Corn Plant for the trial. This material was collected immediately after the gluten thickener. Experimental evaluations were conducted using operating conditions consistent with normal operation of the gluten process in commercial practice. A Westphalia model CA150-01-33 decanter centrifuge was operated using a pump speed of 300 rpm (Watson Marlow model 720S pump); with centrifuge speed of 3900 rpm and centrifuge dam setting of 9, differential setting of 1.0 and 1 Barr backpressure. Five aflatoxin adsorbent clay samples were evaluated. They were Clariant's Sudflock P-63, Tonsil Supreme 526FF, and Toxisorb, and Oil-Dri L-13-394, and L-13-396. Samples were all chosen as they were found to be efficacious at removing over 90% of aflatoxin from gluten samples at the benchtop level. For all clay sources, 0.5% clay was added on a weight/weight basis to liquid gluten. Gluten and adsorbent were then allowed to mix for approximately 10 minutes using an air powered impeller prior to centrifugation. Two samples of overs (clean gluten), and two samples of unders (predominantly clay) were collected from each centrifuge run, with one run being conducted for each experimental clay. Samples were analyzed for moisture, ash, and protein content. In addition gluten loss in the unders fraction was calculated from the ash content of the unders fraction for each adsorbent source. The clay samples were analyzed for mean particle size using a Beckman Coulter analyzer. Furthermore, samples were visually appraised using SEM at resolutions of 50 and 500 um.

The results are presented in Table 3. All clay products had a mean particle size under 200 um with no greater than lx standard deviation relative to the mean particle size. Some were noticeably smaller in mean particle size and more uniform around the mean. The results showed that clay products could be removed from the liquid gluten with no more than 3.85% gluten protein being lost in the process. In a separate bench scale evaluation, the efficacy of mycotoxin adsorption of these clays was evaluated. Clays were tested at 1% wt:wt and the liquid gluten was contaminated with 25 ppb aflatoxin. The results showed that the clays were capable of removing at least 84% of the initial aflatoxin in the liquid gluten.

TABLE 3

Effects of particle size of clay on aflatoxin removal and gluten loss

| Clay product | Mean particle size, um | std dev, um | Gluten loss, % of total gluten | Aflatoxin removed, %* |
|---|---|---|---|---|
| Clariant Sudflock P-63 | 27 | 17 | 3.85 | 100 |
| Oil-Dri L-13-394 | 16 | 13 | 3.54 | 85 |
| Clariant Tonsil Supreme 526FF | 82 | 59 | 3.76 | 100 |
| Oil-Dri L-13-396 | 190 | 137 | 3.90 | 84 |
| Clariant Toxisorb | 33 | 21 | 3.23 | 100 |

*Determined in previous bench-scale investigation using 1% clay added (wt:wt) to liquid gluten containing 25 ppb aflatoxin.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying figures are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The invention claimed is:

1. A process for the removal of mycotoxins from plant-derived proteins comprising:

wet milling corn;

obtaining an ingredient stream comprising liquid corn gluten and a mycotoxin from the wet milling;

forming a mixture comprising said ingredient stream and a particulate mycotoxin sequestering agent;

incubating said mixture to permit adsorption of said mycotoxin to said mycotoxin sequestering agent; and separating said mixture with one or more density-based particle separators to produce a first end-product containing reduced mycotoxins relative to the ingredient stream and a second-end product containing the mycotoxin sequestering agent, wherein said first end-product comprises at least 80% of the plant-derived insoluble proteins and less than 85% of the mycotoxins present in the ingredient stream.

2. The process of claim 1, wherein a total amount of said plant-derived protein in said first end-product is 90% or more of the plant-derived protein contained in said ingredient stream.

3. The process of claim 2, wherein a total amount of said plant-derived protein in said first end-product is 97% percent or more of the plant-derived protein contained in said ingredient stream.

4. The process of claim 1, wherein said mycotoxin includes at least one member selected from the group consisting of aflatoxin, fumonisin, vomitoxin, zearalenone and ochratoxin, and wherein said first end-product has a concentration of mycotoxin that is less than 100 ppb.

5. The process of claim 4, wherein said first end-product has a concentration of mycotoxin of less than 20 ppb.

6. The process of claim 1, wherein said first end-product comprises no more than 55% of said mycotoxins contained in said ingredient stream before contacting with the mycotoxin sequestering agent.

7. The process of claim 1, wherein said first end-product comprises no more than 10% of said mycotoxins contained in said ingredient stream before contacting with the mycotoxin sequestering agent.

8. The process of claim 1, wherein said ingredient stream comprises at least 50% liquid by weight.

9. The process of claim 1, wherein said mycotoxin sequestering agent is selected from the group consisting of adsorbent clays, hydrated sodium/calcium aluminosilicates, and activated charcoals.

10. The process of claim 9, wherein said mycotoxin sequestering agent is an adsorbent clay.

11. The process of claim 10, wherein said adsorbent clay is a bentonite clay.

12. The process of claim 9, wherein said mycotoxin sequestering agent does not contain a flocculating agent.

13. The process of claim 9, wherein said mycotoxin sequestering agent comprises particles having diameters ranging from 20 micrometers to one-quarter inch.

14. The process of claim 9, wherein the diameters of the particles of said mycotoxin sequestering agent range from 100 to 200 micrometers.

15. The process of claim 1, wherein said mycotoxin sequestering agent is between 0.05% and 5% by weight of said mixture.

16. The process of claim 1, wherein said mycotoxin sequestering agent is between 0.5% and 1% by weight of said mixture.

17. The process of claim 1, wherein said density-based particle separators are selected from the group consisting of a centrifuge, a hydrocyclone and combinations thereof.

18. The process of claim 17, wherein said density-based particle separators comprises one or more hydrocyclones connected to a centrifuge, and wherein said separating step comprises:
    first separating said mixture in said hydrocyclones to produce a first hydrocyclone stream comprising said first end-product and a second hydrocyclone stream;
    further separating said second hydrocyclone stream in said centrifuge to produce a first centrifuge stream comprising said first end-product and a second centrifuge stream comprising said second end-product.

19. The process of claim 1, wherein the liquid corn gluten comprises 50% or more of the total protein derived from the corn.

* * * * *